(12) United States Patent
Korenko et al.

(10) Patent No.: US 11,478,557 B2
(45) Date of Patent: Oct. 25, 2022

(54) METHOD OF PREPARING A RADIOACTIVE YTTRIUM PHOSPHATE PARTICLE SUSPENSION

(71) Applicant: Vivos, Inc., Richland, WA (US)

(72) Inventors: Michael Korenko, Pasco, WA (US); David Swanberg, Kennewick, WA (US)

(73) Assignee: Vivos, Inc., Richland, WA (US)

( * ) Notice: Subject to any disclaimer, the term of this patent is extended or adjusted under 35 U.S.C. 154(b) by 0 days.

(21) Appl. No.: 16/459,466

(22) Filed: Jul. 1, 2019

(65) Prior Publication Data

US 2021/0000987 A1    Jan. 7, 2021

(51) Int. Cl.
*A61K 51/02*      (2006.01)
*A61K 51/12*      (2006.01)

(52) U.S. Cl.
CPC ........... *A61K 51/02* (2013.01); *A61K 51/1217* (2013.01)

(58) Field of Classification Search
CPC ............................ A61K 51/02; A61K 51/1217
See application file for complete search history.

(56) References Cited

PUBLICATIONS

Onoda et al., J. Mater. Res. Technol. 2014; 3(2):122-128 (Year: 2014).*

* cited by examiner

*Primary Examiner* — Robert S Cabral
(74) *Attorney, Agent, or Firm* — Indiano Law Group, LLC; F. Victor Indiano; C. John Brannon

(57) ABSTRACT

A method of preparing a radioactive yttrium phosphate particle suspension.

10 Claims, 1 Drawing Sheet

METHOD OF PREPARING A RADIOACTIVE YTTRIUM PHOSPHATE PARTICLE SUSPENSION

FIELD AND BACKGROUND OF THE INVENTION

A method of preparing a radioactive yttrium phosphate particle suspension for the treatment of tumors including solid tumors.

The patents and publications referred to herein are provided herewith in an Information Disclosure Statement in accordance with 37 CFR 1.97.

SUMMARY OF THE INVENTION

The method claimed is the preparation of radioactive yttrium phosphate particles of a size preferred for interstitial application in solid tumors.

BRIEF DESCRIPTION OF THE FIGURES

The foregoing and other features and advantages of the present invention will become more readily appreciated as the same become better understood by reference to the following detailed description of the preferred embodiment of the invention when taken in conjunction with the accompanying drawings, wherein.

Figure 1:
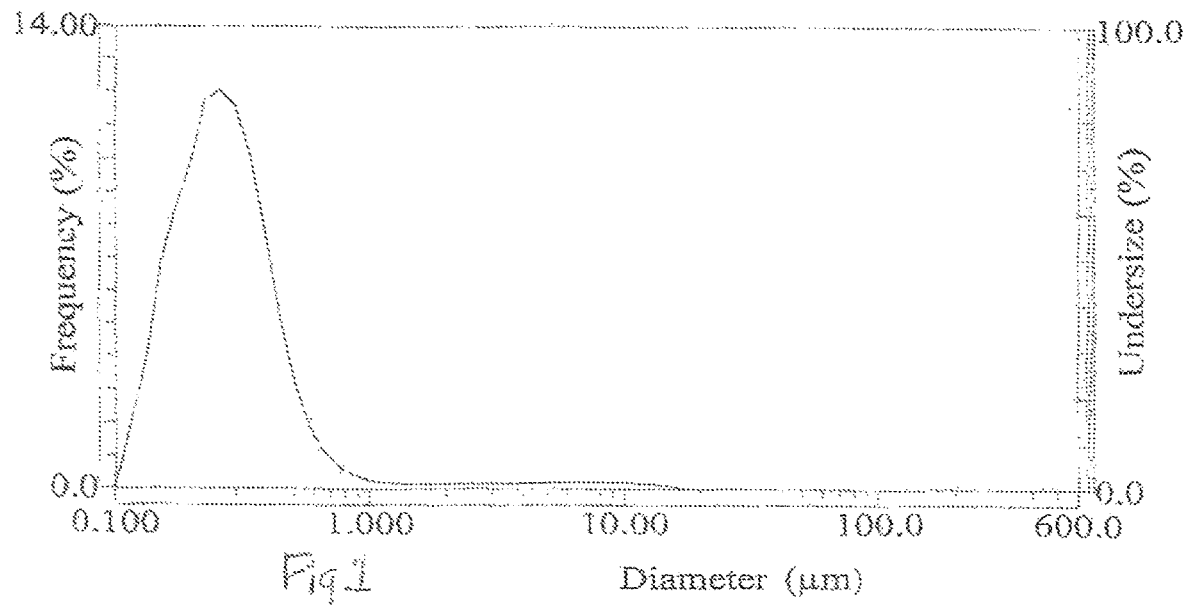
FIG. 1 illustrates particle size determined through the claimed process with pH of 7.35 yielding particle median size of 0.2450 um.
Figure 2:
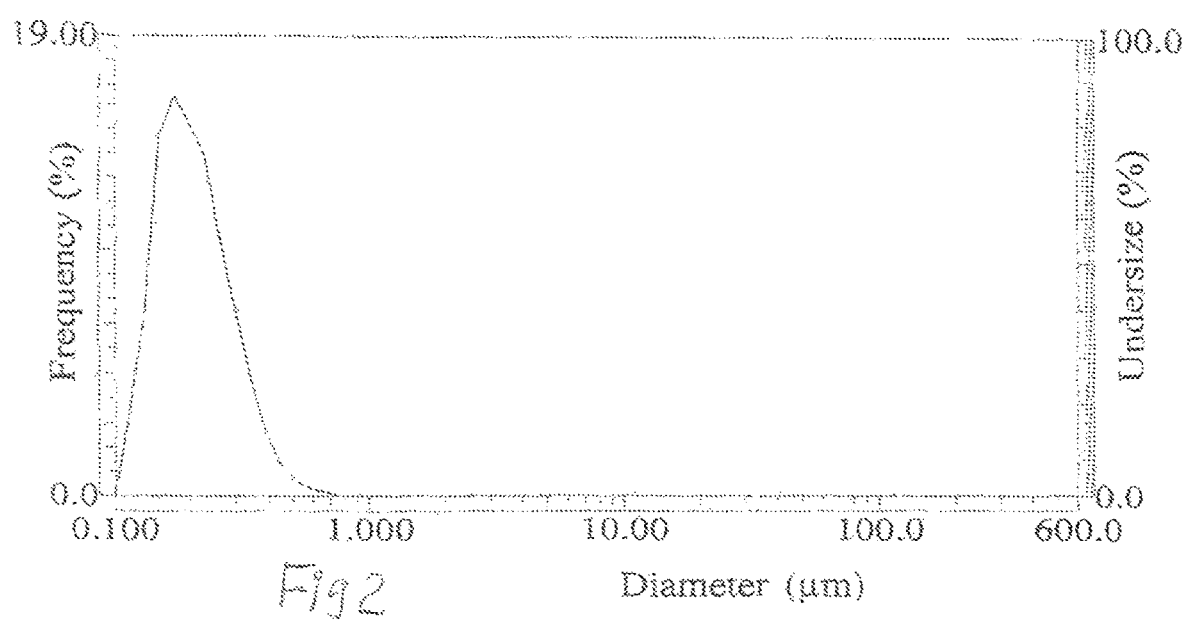
FIG. 2 with pH 7.4 and median particle size of 0.1844 um with particles in each of FIG. 1 and FIG. 2 providing interstitial effectiveness for cell space application.

The foregoing descriptions of specific embodiments of the present invention have been presented for purposes of illustration and description. They are not intended to be exhaustive or to limit the present invention to the precise forms disclosed, and obviously many modifications and variations are possible in light of the above description and figures. The exemplary embodiment was chosen and described in order to best explain the principles of the present invention and its practical application for purposes of enabling others who are skilled in the art and making of the product to best utilize the present invention and various embodiments with various modifications as are suited to the particular use contemplated.

DETAILED DESCRIPTION OF THE INVENTION

A method of preparing a radioactive yttrium salt particle suspension comprising multiple steps comprising: using a hydrothermal process wherein a solution of soluble yttrium salt from the group of yttrium chloride, yttrium nitrate, yttrium sulfate, and yttrium bromide. is combined with a solution of sodium phosphate having a stoichiometric excess of phosphate and pH when combined in the range of 1.5 to 8 and preferably pH in the range of 7 to 8.

Combining the solutions with continuous stirring and rapidly heating in a closed vessel to 150° C. and held for 1 to 10 hours to yield greater than 99.99% conversion of soluble yttrium to insoluble $YPO_4$ and to achieve the desired particle size distribution and;

Creating the desired particle size distribution of $YPO_4$ particles suspended in buffered saline at neutral pH suitable for direct injection into human or animal tissue.

The radioactive particle suspension wherein the particle size is less than 2 um.

The radioactive particle suspension comprised of at least 90 percent of the total particle volume consisting of particles in the range of 0.1 um to 2 um.

And further comprising: wherein the starting concentration of soluble yttrium in the combined solution is in the range of 0.5 to 3.0 mole/liter and the stoichiometric excess of phosphate ranges from 10 to 100%.

And further, comprising: the starting concentration of soluble yttrium in the combined solution is 0.08 moles/liter and the stoichiometric excess of phosphate is 25%.

The method further comprising: the particle suspension formed by preparing the particle precursor solution, mixing and heating to form the $YPO_4$ particles by controlled precipitation followed by post-processing the particles to achieve a suspension of $YPO_4$ particles in phosphate buffered saline solution at neutral pH suitable for injection into human or animal tissue.

The method further comprising: the particle suspension wherein the post processing consists of rinsing the particles 3 times with sterile phosphate buffered saline (PBS) solution and removing or adding PBS to achieve the final desired volume.

The method further comprising: the particle suspension wherein the post processing consists of adjusting the pH of the final solution with sodium hydroxide then removing excess solution or adding sterile PBS to achieve the final desired volume.

The method further comprising: the particle suspension wherein the yttrium phosphate particles are radioactive to serve as distributed sources of therapeutic radiation for treating cancerous tumors and other diseases and: making the particles radioactive by adding a small mass of soluble radioactive isotope to the particle precursor solution that becomes homogeneously incorporated into the insoluble yttrium phosphate particle matrix.

The method further comprising; the yttrium phosphate particle suspension wherein the particle concentration is in the range of 40 mg/ml to 125 mg/ml to facilitate imaging by x-ray computed tomography after being combined in a ratio of 1 to 4 by volume with biocompatible hydrogel or other suitable liquid carrier solution for injection into human or animal tissue.

What is claimed:

1. A method of preparing a radioactive yttrium phosphate particle suspension comprising: using a hydrothermal process, where in a solution of yttrium salts from the group of yttrium chloride, yttrium nitrate, yttrium sulfate, and yttrium bromide is combined with a solution of sodium phosphate having a stoichiometric excess of phosphate and a pH when combined in the range of 1.5 to 8; combining the solutions, with continuous stirring and heating in a closed vessel to the range of 110° C. to 160° C. and held for 1 to 20 hours to yield greater than 99.99% conversion of soluble yttrium to insoluble $YPO_4$ and to achieve a first particle size distribution and; creating the first particle size distribution of $YPO_4$ particles suspended in buffered saline at neutral pH suitable for direct injection into human or animal tissue.

2. The method depending from claim 1 further comprising: the radioactive yttrium phosphate particle suspension wherein the particle size is less than 2 um.

3. The method depending -from claim 2 further comprising: the radioactive yttrium phosphate particle suspension comprised of at least 90 percent of the total panicle volume consisting of p-altides in the range of 0.1 um to 2 um.

4. The method depending from claim 3 and further comprising: wherein a starting concentration of soluble yttrium in the combined solution is in the range of 0.5 to 3.0 mole/liter and the stoichiometric excess of phosphate ranges from 10 to 100%.

5. The method depending from claim 3 and further comprising: a starting concentration of soluble yttrium in the combined solution is 0.08 moles/liter and the stoichiometric excess of phosphate is 2.5%.

6. The method of claim 1 further comprising: mixing and heating the first particle size distribution of $YPO_4$ particles suspended in buffered saline at neutral pH to form the $YPO_4$ particles by controlled precipitation followed by post-processing the particles to achieve a suspension of $YPO_4$ particles in phosphate buffered saline solution at neutral pH suitable for injection into human or animal tissue.

7. The method of claim 6 further comprising: the particle suspension wherein the post processing consists of rinsing the particles 3 times with sterile phosphate buffered saline (PBS) solution and removing or adding PBS to achieve the final desired volume.

8. The method of claim 6 further comprising: the particle suspension, wherein the post processing consists of adjusting the pH of the final solution with sodium hydroxide then removing excess solution or adding sterile PBS to achieve the final desired volume.

9. The method of claim 1 further comprising: the first particle size distribution of $YPO_4$ particles suspended in buffered saline at neutral pH wherein the yttrium phosphate particles are radioactive to serve as distributed sources of therapeutic radiation for treating cancerous tumors and other diseases; and making the particles radioactive by adding a small mass of soluble radioactive isotope to the at least one of the respective solutions of yttrium salts from the group of yttrium chloride, yttrium nitrate, yttrium sulfate, and yttrium bromide, solution of sodium phosphate, and combinations thereof that becomes homogeneously incorporated into the insoluble yttrium phosphate particle matrix.

10. The method of claim 1 further comprising: the yttrium phosphate particle suspension of claim 4 wherein particle concentration is in the range of 40 mg/ml to 12.5 mg/ml to facilitate imaging by x-ray computed, tomography after being combined in a ratio of 1 to 4 by volume with biocompatible hydrogel or other suitable liquid carrier solution and injection into human or animal tissue.

* * * * *